(12) United States Patent
Heinen

(10) Patent No.: US 6,730,773 B2
(45) Date of Patent: May 4, 2004

(54) SALT OF A MELAMINE CONDENSATION PRODUCT AND A PHOSPHOROUS-CONTAINING ACID

(75) Inventor: Wouter Heinen, BC Maastricht (NL)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/182,075
(22) PCT Filed: Jan. 15, 2001
(86) PCT No.: PCT/NL01/00024
§ 371 (c)(1), (2), (4) Date: Oct. 15, 2002
(87) PCT Pub. No.: WO01/57051
PCT Pub. Date: Aug. 9, 2001

(65) Prior Publication Data
US 2003/0096946 A1 May 22, 2003

(30) Foreign Application Priority Data
Jan. 31, 2000 (NL) .............................................. 1014232

(51) Int. Cl.[7] .................................................. C08G 79/02
(52) U.S. Cl. ........................ 528/398; 528/422; 528/423
(58) Field of Search ................................. 528/398, 422, 528/423

(56) References Cited

FOREIGN PATENT DOCUMENTS

| EP | 363321 | 4/1990 |
|---|---|---|
| EP | 466137 | 1/1992 |
| EP | 475367 | 3/1992 |
| FR | 2620715 | 3/1989 |
| WO | 96/16948 | 6/1996 |
| WO | 99/02606 | 1/1999 |
| WO | 00/02869 | 1/2000 |

*Primary Examiner*—Samuel A. Acquah
(74) *Attorney, Agent, or Firm*—Tyler A. Stevenson

(57) ABSTRACT

Salt of a melamine condensation product and a phosphorus-containing acid, the phosphorus-containing acid being a monobasic phosphorus-containing acid. Further a method for the preparation of a phosphorus-containing salt of a melamine condensation product in which a triazine compound and a monobasic phosphorus-containing acid are heated together to a temperature between 250 and 400° C.

10 Claims, No Drawings

SALT OF A MELAMINE CONDENSATION PRODUCT AND A PHOSPHOROUS-CONTAINING ACID

The invention relates to a salt of a melamine condensation product and a phosphorus-containing acid, a method for the preparation of this salt and the use thereof as a flame retardant in flame-retardant polymer compositions.

The use of the combination of a melamine condensation product and a phosphorus compound in flame-retardant polymer compositions is known from NL-B-1006525. Said patent describes a flame-retardant polyester composition in which a nitrogen-containing compound and a phosphorus-containing compound form the flame-proofing combination. The disadvantage of the polymer composition according to NL-B-1006525 is that the phosphorus-containing compound and the nitrogen-containing compound must be prepared separately. As the nitrogen-containing compound in NL-B-1006525 use is made inter alia of melam. However, the preparation of almost pure melam is a multi-step process that is difficult to carry out and economically little attractive. In a first step melamine and a catalyst are used to form a salt of melam and the relevant catalyst. From this salt almost pure melam is to be obtained in a number of subsequent steps. Known catalysts mentioned in the literature are zinc chloride and sulphonic acids such as paratoluene sulphonic acid.

The object of the invention is to obtain a flame retardant on the basis of a melamine condensation product and a phosphorus-containing compound which can be prepared in an economic way in a single process step. In particular the object of the invention is to obtain a flame retardant on the basis of melam and a phosphorus-containing compound which can be prepared in an economic way in one single process step.

It has been found that this object is attained by preparing a phosphorus-containing salt of a melamine condensation product and a phosphorus-containing acid while using a monobasic phosphorus-containing acid as the phosphorus-containing acid. Melam is preferably used as the melamine condensation product.

Monobasic phosphorus-containing acids that are applicable in the present invention are compounds that contain at least a phosphoric acid, phosphonic acid or phosphinic acid group possessing only one acid equivalent.

Examples of phosphoric acid, phosphonic acid or phosphinic acid groups that possess only one acid equivalent are phosphate ester groups that can be represented by the general formula (I), alkyl phosphonic acid esters that can be represented by the general formula (II) and phosphinic acids that can be represented by the general formula (III):

(R₁O—)(R₂O—)—P(=O)—OH   (I)

(R₃O—)R₄P(=O)—OH,   (II)

R₅R₆P(=O)—OH,   (III)

in which $R_1$ up to and including $R_6$ represent substituted or non-substituted alkyl, aryl, cycloalkyl, aralkyl or alkaryl substituents.

Preferably compounds are used that contain groups according to formula (II) and/or formula (III). Examples of suitable phosphinic acids according to formula (III) are ethylmethylphosphinic acid, diethylphosphinic acid, diethylphosphinic acid, a substituted or non-substituted 1-hydroxydihydrophospholoxide, a substituted or non-substituted 1-hydroxyphospholane oxide and diphosphinic acids. Diphosphinic acids are compounds with two phosphinic acid groups. Examples of suitable phosphonic acid esters according to formula (II) are the methyl, ethyl and propyl ester of methylphosphonic acid.

The phosphorus-containing salt of the monobasic phosphorus-containing acid and the nitrogen-containing compound comprises at least 50–95 mol % of a melamine condensation product, in particular melam.

In EP-A-363,321 a melamine phosphonate or dimelamine phosphonate is described and applied as a flame retardant in polymer compositions. The disadvantage of these salts is that it contains melamine, which can sublime during processing into polymer compositions. The method of preparing these salts stated in EP-A-363,321 is not applicable to condensation products of melamine, such as melam, due to the poor solubility of these in water.

Applicant has also found that the preparation of the phosphorus-containing salt of a melamine condensation product, in particular melam, can be carried out simply by heating a triazine compound and the monobasic phosphorus-containing acid together to a temperature between 250 and 400° C., preferably between 280° C. and 350° C. Suitable triazine compounds are melamine, ammeline and ammelide or mixtures of these. Preferably melamine is used. Impurities such as urea, dicyanodiamide, guanidine and ureidomelamine can be present without objection.

The quantity of monobasic phosphorus-containing acid used amounts to 0.05–0.5 mole per mole of triazine compound. Preferably, 0.1–0.5 mole is used. The monobasic phosphorus-containing acid can also be used in the form of its ammonium or melamine salt. When its melamine salt is used, allowance shall be made for the possible participation of the melamine in a condensation reaction, for instance to melam. The quantity of triazine compound metered to the reactor can be reduced accordingly.

The reaction is carried out by heating a mixture comprising a triazine compound and a monobasic phosphorus-containing acid, or the melamine or ammonium salt of it, to around 250–350° C. Preferably the reaction is carried out between 280 and 320° C. Preferably the reaction is carried out in an almost horizontal stirred reactor. During the reaction ammonia is formed, which can be removed by purging the reactor with an inert gas such as for example nitrogen. Besides melam, whether or not in the form of a phosphorus-containing salt, also small quantities of other triazine condensation products, such as for example melem, melon and methon, whether or not in the form of a phosphorus-containing salt can be formed during the reaction. It is also possible for a small part of the monobasic phosphorus-containing acid to be converted to an anhydride compound.

If desired the phosphorus-containing salt of the melamine condensation product, in particular melam, can be treated further. This further treatment is preferably scrubbing with water so that a part of the melamine and/or other water-soluble components dissolve and are removed from the phosphorus-containing salt of the melamine condensation product.

Applicant has also found that the phosphorus-containing salt of melam according to the invention brings about flame retardancy of polymer compositions.

The polymer composition then comprises, besides the phosphorus-containing salt of the melamine condensation product, in particular melam, at least a polymer. In addition it can comprise reinforcing agents and/or fillers and/or compounds having a synergistic effect for the phosphorus-containing salt of melam can contain compounds and/or flame-retardant components other than those according to the invention. Also the usual additives can further be present, such as for example heat and UV stabilizers, release agents, flow-promoting agents, plasticisers, lubricants, dispersing agents, dyestuffs and/or pigments, in quantities that are generally applicable for these additives insofar as the properties are not adversely influenced.

Polymer compositions that can be made flame-retardant with the phosphorus-containing salt of melam, contain polymers that require heat-resistant flame retardants, such as for example polyamides, polyimides, polyesters, polyurethanes and mixtures and blends of these materials.

Examples of polyamides are polyamides and copolyamides which are derived from diamine and dicarboxylic acids and/or of amino carboxylic acids or the corresponding lactams, such as polyamide 4, polyamide 6, polyamide 6/6,4/6, partially aromatic (co)polyamides, for example polyamides based on an aromatic diamine and adipic acid; polyamides prepared from an alkylene diamine and iso-and/or terephthalic acid and copolyamides thereof, etc.

Examples of polyester are polyester, derived from dicarboxylic acids and dialcohols and/or from hydroxycarboxylic acids or the corresponding lactones such as polyethylene terephthalate, polybutylene terephthalate, poly-1,4-dimethylolcyclohexane terephthalate, polycaprolacton and copolyesters thereof, etc.

Preferably the phosphorus-containing salt of melam is used in polymer compositions with polyethylene terephthalate and/or polybutylene terephthalate, with polybutylene terephthalate being specially preferred, or with polyamides such as nylon-6, nylon 6,6 or nylon 4,6.

If reinforcing agents and/or fillers are used in the polymer composition, the content of these can vary between broad limits and this content is determined in part by the level of mechanical properties that one wants to attain. In general the reinforcing agents content will amount to no more than 50 wt. % of the total polymer composition. Preferably a reinforced polymer composition will contain 5–50 wt. % reinforcing agents, more preferably 15–45 wt. %. Examples of reinforcing agents are mica, clay, talc, glass fibres, aramid fibres and carbon fibres. Different reinforcing agents can be combined. However, glass fibres are preferred.

The flame-retardant property of the polymer composition can be strengthened by the presence of a compound that has synergistic effects for the phosphorus-containing salt of melam. As a consequence the content of the phosphorus-containing salt of melam according to the invention can generally be chosen lower. An example of a compound with a synergistic effect is a char-forming compound, whether or not in combination with a catalyst promoting the formation of char. As char-forming compounds in principle all known substances are eligible that can strengthen the flame-retardant properties of flame-retardant polymer compositions by means of the formation of char caused by the fire. Examples of these are phenol resins, epoxy resins, melamine resins, alkyd resins, silicone resins, urethane resins, polyphenylene ether, polyvinyl alcohol, poly (ethylene-co-vinyl) and compounds with at least two hydroxyl groups. Examples of compounds with at least two hydroxyl groups are alcohols with at least two hydroxyl groups, for example pentaerythritol, dipentaerythritol, tripentaerythritol and mixtures of these. The concentration of the char-forming compound with a synergistic effect for the phosphorus-containing salt of melam is in general between 0 and 30 wt. %. of the total polymer composition.

As a catalyst promoting the formation of char use can be made of, inter alia, metal salts of tungstic acid, a complex acid oxide of tungsten with a metalloid, salts of tin oxide, ammonium sulphamate and/or the dimer thereof. Metal salts of tungstic acid are preferably alkali metal salts of tungstic acid and in particular sodium tungstate. A complex acid oxide of tungsten with a metalloid is understood to be complex acid oxides which are formed from a metalloid such as silicon or phosphorus and tungsten such as silicotungstic acid or phosphotungstic acid. The quantity of catalyst promoting the formation of char that is used in the polymer composition amounts to 0.1–5 wt %, preferably 0.1–2.5 wt %.

The flame-retardant properties of the phosphorus-containing salt of melam according to the invention can be further strengthened when the polymer composition comprises one or more other flame-retardant components. As flame-retardant component in principle all known flame retardants are eligible. Examples of these are antimony oxides, such as for example antimony trioxide, in combination with halogen compounds; alkaline-earth metal oxides, for example zinc oxide, magnesium oxide; other metal oxides, for example alumina, silica, iron oxide and manganese oxide; metal hydroxides, for example magnesium hydroxide and aluminium hydroxide; nano composites; clay such as for example montmorillonite clay and kaolin clay; treated clay such as clay treated with primary ammonium compounds or with quaternary ammonium compounds or with melamine or with phosphorus-containing compounds; silicon-containing compounds such as for example silicates, organosilicon compounds, aromatic organosilicon compounds and silanes; metal borates, for example hydrated or non-hydrated zinc borate; sulphur-containing compounds such as for example zinc sulphide, ammonium sulphate, ammonium sulphamate and melamine sulphate; phosphorus-containing compounds such as for example phosphates, phosphonates, phosphinates, phosphines, phosphine oxides and phosphites. Examples of phosphates are aromatic orthophosphate esters such as for example tris (p-cresyl) phosphate and tris (p-tert-buytyl phenyl) phosphate, Fyrolflex RDP® (AKZO-Nobel) cyclic phosphate esters, tetraphenylbisphenol-A diphosphate, as well as mixtures of the above-mentioned phosphates. Examples of phosphonates are phosphonate esters and mixed phosphonate esters. Further examples of phosphonates are 1,3,2-dioxaphosphorinane-5,5-dimethyl-2-phenoxy-2-oxide, polymeric pentaerythrityl phospohonates such as for example poly [3(-9) alkylene-2,4,8,10-tetraoxa-3,9-diphosphaspiro [5,5] undecane-3,9-dioxide], cyclic phosphonate esters, bicyclic phosphonate esters such as for example pentaerythrityl diphosphonates, the linear or cyclic esters of trimethylolpropane and methylphosphonic acid, such as for example Antiblaze® 1045 LV (Albright & Wilson), cyclic neopentylene pentaerythritol alcohol phosphate. Examples of phosphinates are phosphinate salts such as for example alicylic phosphinate salts and phosphinate esters. Further examples of phosphinates are diphosphinic acids, dimethylphosphinic acid, ethylmethylphosphinic acid, diethylphosphinic acid, and the salts of these acids, such as for example the aluminium salts and the zinc salts. Examples of phosphine oxides are isobutylbis (hydroxyalkyl) phosphine oxide and 1,4-diisobutylene-2,3,5,6-tetrahydroxy-1,4-diphosphine oxide or 1,4-diisobutylene-1,4-diphosphoryl-2,3–5,6-tetrahydroxycyclohexane. Further examples of phosphorus-containing compounds are NH1197® (Great Lakes), NH1511® (Great Lakes), NcendX P-30® (Albemarle), Hostaflam OP5500® (Clariant), Hostaflam OP910® (Clariant) and Cyagard RF 1204®, Cyagard RF 1241® and Cyagard RF 1243® (Cyagard are products of Cytec Industries). Preferably phosphates, phosphinates and/or phosphonates are used as the phosphorus-containing compound. The content of phosphorus-containing compound can vary between 0 wt. % and 25 wt. % of the total of the flame-retardant mixture.

Other known compounds present in flame-retardant compositions, such as the antidrip agent polytetrafluorethylene, can also be present.

The content of other flame-retardant components used in the polymer composition can vary between broad limits but in general is not more than the content of phosphorus-containing salt of melam.

The polymer composition according to the invention can be prepared using the conventional techniques that are known in themselves, by for example dry-mixing all or a number of components in a tumbler mixer, followed by melting in a melt mixer, for example a Brabender mixer or a single- or twin-screw extruder or a kneader. Preferably a twin-screw extruder is used.

The different components of the polymer composition can be metered together to the throat of the extruder. They can be also metered to the extruder at different places. A number of the components that may be present, such as for example dyestuffs, stabilizers, the flame-retardant composition, compounds with a synergistic effect for the triazine flame retardant and/or other flame-retardant components, can be added to the polymer for example in the form of a masterbatch.

The flame-retardant polymer composition according to the invention can be processed with techniques known to one skilled in the art, for example injection moulding, to form semi-finished products or final products.

The invention is explained further on the basis of the following examples:

EXAMPLE 1

In a 4 litre reactor a mixture of 400 g melamine and 170 g ethylmethylphosphinic acid $(CH_3\_)(CH3CH2\text{---})P(\text{==}O)\text{---}OH)$ is introduced. The reactor is heated to 290° C. in two hours. The ammonia formed is removed by means of a nitrogen gas flow. The reaction mixture is heated for another hour, after which the product is cooled off. According to HPLC analysis the product contains 67 wt. % melam and 1 wt. % melamine. According to elementary analysis the phosphorus content of the product is 9 wt. %, which corresponds to an ethylmethylphosphinic acid content of $0.5.10^2$ mol %.

EXAMPLE 2

A 4 litre reactor is charged with a mixture of 400 g melamine and 175 g methylmethylphosphonic acid $(CH_3\text{---})(CH_3O\text{---})P(\text{==}O)\text{---}OH)$. The reactor is heated to 290° C. in two hours. The ammonia formed is removed by means of a nitrogen gas flow. The reaction mixture is heated for another hour, after which the product is cooled off. According to HPLC analysis the product contains 66 wt. % melam and 2 wt. % melamine. According to elementary analysis the phosphorus content of the product is 9 wt. %, which corresponds to a methylmethylphosphonic acid content of $0.5.10^2$ mol %.

EXAMPLE 3

A co-rotating twin-screw extruder (Werner & Pfleiderer, type ZSK 30/33) was fed with: 45 parts of polybutylene terephthalate, 30 parts of glass fibre, 25 parts of the product of example 1. The barrel temperature was set to 250° C. and the screw speed to 200 revolutions per minute. From the compounds obtained test rods with a thickness of 1.6 mm were made. A set of test bars was made which was subjected to the UL94 fire test. The fire behaviour classification was VO. The E-modulus of the test bars was 10.0 MPa and the elongation at failure in each case was 2.0% (ISO 527/1).

EXAMPLE 4

A co-rotating twin-screw extruder (Werner & Pfleiderer, type ZSK 30/33) was fed with: 45 parts of polybutylene terephthalate, 30 parts of glass fibre, 8 parts of Antiblaze ® 1045 (Albright & Wilson) and 17 parts of the product of example 1. The barrel temperature was set to 250° C. and the screw speed to 200 revolutions per minute. From the compounds obtained test bars with a thickness of 1.6 mm were made. A set of test bars was manufactured which was subjected to the UL94 fire test. The fire behaviour classification is VO. The E-modulus of the test bars was 10.3 MPa and the elongation at failure in each case was 2.1% (ISO 527/1).

EXAMPLE 5

A co-rotating twin-screw extruder (Werner & Pfleiderer, type ZSK 30/33) was fed with: 45 parts of polybutylene terephthalate, 30 parts of glass fibre, 8 parts of aluminium ethylmethylphosphinate, 17 parts of the product of example 1. The barrel temperature was set to 250° C. and the screw speed to 200 revolutions per minute. From the compounds obtained test bars with a thickness of 1.6 mm were made. A set of test bars was made which was subjected to the UL94 fire test. The fire behaviour classification is VO. The E-modulus of the test bars was 10.3 MPa and the elongation at failure in each case was 2.1% (ISO 527/1).

EXAMPLE 6

A small-scale mini-extruder (self-built) was fed with: 75 parts of polybutylene terephthalate and 25 parts of the product of example 2. The barrel temperature was set to 270° C. and the screw speed to 100 revolutions per minute. From the compounds obtained test bars with a thickness of 2.0 mm were made. A set of test specimens was made which was subjected to the UL94 fire test. The fire behaviour classification is VO.

EXAMPLE 7

A small-scale mini-extruder (self-built) was fed with: 75 parts of polyamide-6 and 25 parts of the product of example 2. The barrel temperature was set to 270° C. and the screw speed to 100 revolutions per minute. From the compounds obtained test bars with a thickness of 2.0 mm were made. A set of test specimens was made which was subjected to the UL94 fire test. The fire behaviour classification is VO.

What is claimed is:

1. Salt of a melamine condensation product and a phosphorus-containing acid, characterized in that a monobasic phosphorus-containing acid is used as the phosphorus-containing acid.

2. Salt according to claim 1, characterized in that the monobasic phosphorus containing acid is a compound that at least contains: a phosphoric acid, phosphonic acid or phosphinic acid group which possess only one acid equivalent.

3. Salt according to claim 1, characterized in that alkyl phosphonic acid esters or phosphinic acids are used as the monobasic phosphorus-containing acid.

4. Salt according to claim 1, characterized in that melam is used as melamine condensation product.

5. Method for the preparation of a phosphorus-containing salt of a melamine condensation product, characterized in that a triazine compound and a monobasic phosphorus-containing acid are heated together to a temperature between 250° and 400° C.

6. Method according to claim 5, characterized in that the temperature is between 280° C. and 350° C.

7. Method according to claim 1, characterized in that melamine, ammeline and/or ammelide are used as the triazine compounds.

8. Method according to claim 7, characterized in that melamine is used as the triazine compound.

9. Method according to claim 1, characterized in that use is made of phosphonic acid esters or phosphinic acid as the monobasic phosphorus-containing acid.

10. Polymer composition comprising a salt of a melamine condensation product and a monobasic phosphorus-containing acid.

* * * * *